United States Patent [19]

Hagel et al.

[11] Patent Number: 4,620,046
[45] Date of Patent: Oct. 28, 1986

[54] NITRATED ARYL ETHERS

[75] Inventors: Rainer Hagel, Lichtenfels; Klaus Redecker, Nuremberg, both of Fed. Rep. of Germany

[73] Assignee: Dynamit Nobel Aktiengesellschaft, Troisdorf, Fed. Rep. of Germany

[21] Appl. No.: 748,027

[22] Filed: Jun. 24, 1985

Related U.S. Application Data

[63] Continuation of Ser. No. 477,424, Mar. 21, 1983, abandoned.

[51] Int. Cl.$^4$ .............................................. C07C 79/10
[52] U.S. Cl. .................................... 568/930; 149/105; 568/586; 528/86; 528/210
[58] Field of Search .................. 149/105; 528/86, 210; 568/586, 930

[56] References Cited

U.S. PATENT DOCUMENTS

| | | | |
|---|---|---|---|
| 3,894,086 | 7/1975 | Lerom et al. | 568/586 |
| 3,944,575 | 3/1976 | Villaescusa et al. | 568/306 |
| 4,201,853 | 5/1980 | Henry et al. | 149/105 |
| 4,214,086 | 7/1980 | Fäh | 546/290 |
| 4,250,294 | 2/1981 | Hagel et al. | 586/586 |

OTHER PUBLICATIONS

Kuboszek et al., Chem. Abst., vol. 96, 122407r, p. 661 (1982), Abst. of Pol. PL 109577, issued Apr. 30, 1981.

*Primary Examiner*—Stephen J. Lechert, Jr.
*Assistant Examiner*—Anne Brookes
*Attorney, Agent, or Firm*—Antonelli, Terry & Wands

[57] ABSTRACT

A nucleus-nitrated aryl ether is produced by reacting an aromatic halogen-containing nitro compound with an aromatic hydroxy compound, which may be nitrated in the presence of a base. The ether may be an oligomer compound or a polymer and is suitable for use as an explosive or propellant charge.

2 Claims, No Drawings

NITRATED ARYL ETHERS

This is a continuation of application Ser. No. 477,424, filed Mar. 21, 1983, now abandoned.

This invention relates to nucleus-nitrated aryl ethers having at least three benzene rings as a structure element wherein at least one of the benzene rings contains up to three nitro groups and to a process for the preparation of these nitrated aryl ethers by nucleophilic substitution of the halogen atom in aromatic halogen nitro compounds with suitable aromatic hydroxy compounds in the presence of basic media.

The preparation of polynitro aryl ether compounds by conversion of monohydroxy aryls or dihydroxy aryls or by conversion of phenols with nitrochlorobenzols in the presence of alkali is, for example, described in U.S. Pat. No. 3,944,575 or in C.A. 85, 159665 (1975). An application of these low nitrated ethers as explosives is not disclosed.

A highly nitrated aryl ether is produced, for example, from the reaction of 1,3-dichloro-4,6-dinitrobenzol with resorcinol or hydroquinone.

These ethers are cyclic ethers. With the successive nitration, there is obtained a thermally stable octanitro ether which is proposed as explosive.

A disadvantageous feature of this well-known method is that products are obtained thereby with which a maximum of only two nitro groups are present in each benzene ring. These nitro groups must supply oxygen required for the satisfactory reaction of an explosive, more particularly in the presence of binders and determine the explosion heat. In addition, owing to a subsequent nitration reaction, a further introduction of nitro groups is almost impossible so that these well-known products contain too little oxygen for an application as explosive substance. The task of the present invention was, for this reason, to find a way to form new aromatic compounds which possess, at the most, three nitro groups per benzene ring.

Further, there was the task of preparing a thermally stable explosive substance which can, alone or in the presence of binding agents, replace the previously customary propellant charges such as the nitric acid ester of cellulose or polyvinyl alcohol. These well-known propellant charges have the disadvantage that temperatures under 200° C. already bring these substances to self-ignition so that these propellant charges are, for this reason, unsuitable with the effect of higher temperatures which, more particularly, occur in space travel or with weapons having a high firing rate.

The polynitro aryl ethers of this invention have been discovered to satisfy this task. These ethers have decomposition temperatures above 200° C. and are suitable as explosives or propellant charges. They possess, in part, the optimum number of three nitro groups per benzene ring.

The preparation of these new compounds takes place by reaction of aromatic halogen-containing nitro compounds with aromatic hydroxy compounds. Preferentially, these compounds originated from trinitro halogen benzols. By reaction with dihydroxy benzene in this way, polynitro polyphenylene oxides are produced in the presence of basic media and by successive nitration, a maximum of two further nitro groups can be introduced on the dihydroxy benzene structural element.

It is important that one of the two reactants is substituted by two hydroxyl groups or two halogen atoms. For this reason, it is possible to employ both dichloropolynitro benzols as well as dihydroxy nitro benzene as one of the initial reactants. The other reactant must then have the corresponding grouping required for progress of the reaction. It is accordingly possible in accordance with the invention to react both an aromatic dihydroxy compound with an aromatic monochloro compound or even an aromatic dichloro compound with a monohydroxy compound provided oligomer compounds are to be obtained. At least one of the reactants should, nevertheless, have three nitro groups per benzene ring if especially high energy compounds are to be obtained.

It is, nevertheless, also possible in accordance with the invention to react an aromatic nitrated dichloro compound with an aromatic, if necessary nitrated, dihydroxy compound. In this case, long-chained polynitro polyphenylene oxides with molar weights between 450 and about 3000 are obtained.

The reaction components are substituted in stoichiometric relationships in such a way that an equivalent of the monohydroxy compound or 0.5 equivalent of the dihydroxy compound is reacted, preferentially, per halogen atom. The hydroxy compound can also be employed in an excess of 5 to 10%; for example, 2 moles of picryl chloride can advantageously be reacted with 1.1 mole of a dihydroxy benzene.

The reaction is carried out in the presence of a base as, for example, an alkali hydroxide which can be dissolved in water. The quantity of the base corresponds to the OH-acid hydrogen component and is, likewise, substituted advantageously in an excess of about 10%.

Effecting the reaction of the halogen polynitro aromatic compounds with the hydroxy aromatic compounds which, if necessary, can be nitrated, is generally undertaken with the reactive components being dissolved in a solvent, and the base is added while being cooled at ambient temperature or while boiling the solvent. Suited for this reaction are solvents miscible with water, such as ketones, for example, acetone, or DMF (dimethylformamide), DMSO (dimethylsulfoxide) and alcohols, including also solvents with limited miscibility with water, such as for example, methylacetate.

After a completed reaction, the raw product is precipitated by the addition of water, the solvent is removed and the precipitate is washed and dried. The resulting product can be used directly in this form as, in part, a high-temperature resistant propellant charge or subjected to a further nitrating, for example, with fuming nitric acid. This further nitration is carried out, preferentially with polymers, such that the partially nitrated aryl ether is suspended within concentrated sulfuric acid. Fuming nitric acid is slowly added to this suspension. At the same time, too strong a heating of the reaction mixture is to be avoided by stirring and/or by the rate of the addition of the nitric acid. The reaction temperature should, if possible, not exceed 30° C.

The reaction proceeds surprisingly smoothly although the intrinsically the same reaction of, for example, pictryl chloride to form the corresponding nitrated diphenyl ethers, in general, only takes place properly with a prepared phenolic metal salt. The alkali metals, or silver, are suitable as metals for preparation of metal phenolates. Work must be frequently carried out in this case in a medium having no water.

Among the halogen-containing nitro compounds which can be used according to the invention are such which are derived from aromatic compounds, there can be named, for example, the mono- or dihalogen compounds of the di- and trinitro benzene or the di- or trinitro benzenes such as 2,4,6-trinitro-3,5-dichlorotoluene or the chlorodinitro and trinitro benzenes or 2,4,6-trinitro-3,5-dichloroanisole.

Among the two-nucleous (dinuclear) aromatic compounds which can be used as initial reactants for the new nitro ethers are included, for example, dichloropolynitro compounds of diphenyl whereby the two rings of the diphenyl can also be connected with each other through heteroatoms such as, for example, through oxygen, nitrogen or a group from the series —NH—, —NH—CO—CO—NH— or —CH=CH—. These compounds can be characterized by the general formula:

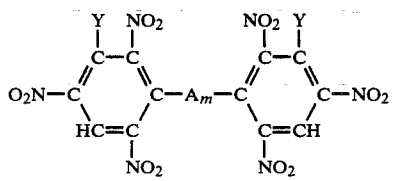

in which A represents oxygen, nitrogen or a radical selected from the group consisting of —CH=CH—,

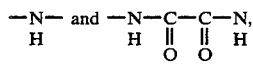

Y represents a halogen and m is 0 or 1.

As examples, can be named 3,3'-dichloro-2,4,6,2',4',6'-hexanitrodiphenyl, dichlorohexanitrostilbene or dichlorohexanitrodiphenylamine. As multinuclear initial compounds, there can further be named, for example, the dihalogen polynitro compounds of naphthalene, anthracene or phenanathrene.

The aromatic hydroxy compounds which can be used according to the invention are derived similarly as the chloronitro compounds from mono- or poly-nuclear aromatic compounds which, if necessary, can also be condensed with one another. As examples for single-nucleus (mononuclear) aromatic hydroxy compounds, there can be named phenol as well as nitrophenols, pyrocatechine, resorcinol or hydroquinone and their nitro compounds as well as corresponding derivatives of toluene or anisole. For example, naphthols or dihydroxy diphenyls as well as their nitro derivatives can be named as suitable polynuclear aromatic hydroxy compounds.

The nitrated aryl ethers obtained according to the present invention possess, in part, a remarkably high thermal stability. Owing to their higher energy content and the improved oxygen balance as opposed to previously known nitrated aromatic compounds, these ethers can be used as a propellant charge for high thermal requirements. The following describes more in detail the preparation of these compounds.

First Steps of Preparation

Picryl Chloride

In this procedure, 229 g of dry picric acid is added, while stirring, to 140 ml of POCL₃ and 100 ml of pyridine is added dro-by-drop without cooling. The temperature rises to 75°–80° C. Thereafter, there is a treatment for one-half an hour at 90° C. in an oil bath and, following this treatment, the solution is cooled down to about 40° C. and stirred in 3 liters of water with Turrax stirrers and then poured. After filtration, the residue is washed free of acid and dried. The yield is 240 g (97% of theory) F (flow point): 79° up to 81° C.

Styphnic Acid Dichloride

In portions 730 g (1.81 mole) of dipyridiniumstyphnate is added while stirring to 350 ml (3.82 mole) of POCl₃ (initially without cooling). The temperature thereby increases and is kept by cooling to 70° C. After the complete addition of the salt, the solution is kept for 30 minutes at 100° C. with continued stirring and, following this, the solution is then cooled down to 40° to 50° C. and the mixture is broken up by portion-wise introduction into 3 liters of water while stirring vigorously. The water temperature is kept at 30° C. by the addition of ice. After filtering with suction, the residue is washed free of acid and air-dried.

Yield: 480 g (94.0% of theory) F: 122° to 126° C.

EXAMPLES 1–3

Bis-(trinitrophenoxy)-benzenes 495 g (2 moles) of picryl chloride and 121 g (1.1 mole) of a dihydroxy benzene such as:

Example 1: Pyrocatechine
Example 2: Resorcinol
Example 3: Hydrochinone are dissolved in 1 liter of acetone (in the case of hydrochinone in 1.3 liters of acetone) and mixed, drop-by-drop, with vigorous stirring at 20° C. under cooling (in the case of pyrocatechine at boiling temperature) with 88 g (2.2 moles) NaOH in water (1:1). Stirring continues for 15 minutes more and following this, 4 liters of water are added drop-by-drop. The solid component is separated out using water and then washed and dried with ethanol.

Yields:

1,2-bis-(2',4',6'-trinitrophenoxy)benzene 346 g (65% of theory)

1,3-bis-(2',4',6'-trinitrophenoxy)benzene 479 g (90% of theory)

1,4-bis-(2',4',6'-trinitrophenoxy)benzene 480 g (90% of theory)

The compounds obtained have the following properties:

| | | | Properties | | |
| --- | --- | --- | --- | --- | --- |
| | | | Friction | Percussion | |
| | F | Vp | Sensitivity | | EW |
| Compound | (°C.) | (°C.) | (N) | (J) | (J/g) |
| 1,2-Bis-TNPB | 235–238 | 320 | >350 | 8 | 2850 |
| 1,3-Bis-TNPB | 188–190 | 320 | >350 | 8 | 2970 |
| 1,4-Bis-TNPB | >350 | 320 | >350 | 8 | 2850 | in which:
F=flow point
V_p=deflagration point
EW=explosion heat.
TNPB=(2',4',6'-trinitrophenoxy)benzene

EXAMPLES 4–6

In these examples, 282 g (1 mole) styphnic acid dichloride and 278 g (2 moles) of a nitrophenol such as:

Example 4: 2-nitrophenol
Example 5: 3-nitrophenol

Example 6: 4-nitrophenol
are dissolved in 1 liter of acetone and mixed, drop-by-drop, with vigorous stirring with 80 g (2 moles) NaOH in water (1:1) at a temperature of 20° C. under cooling. Subsequently, the procedure is as described in Examples 1 to 3.

Yields:

1,3-bis-(2'-nitrophenoxy)-2,4,6-trinitro benzene 404 g (83% of theory) F: 265°–268° C.

1,3-bis-(3'-nitrophenoxy)-2,4,6-trinitro benzene 141 g (29% of theory) F: 180°–182° C.

1,3-bis-(4'-nitrophenoxy)-2,4,6-trinitro benzene 405 g (83% of theory) F: 223°–227° C.

EXAMPLE 7

The procedure is carried out as described in Example 3 although, with application of 1.3 l dimethylformamide instead of the acetone, as a solvent and 480 g yield is obtained (90% theory).

EXAMPLE 8

The reaction according to Example 3, although with 170 ml pyridine, leads to a yield of 420 g (79% of theory).

EXAMPLE 9

The reaction according to Example 3, however, with 240 ml triethylamine as base instead of sodium hydroxide solution, results in 480 g yield (90% of theory).

EXAMPLE 10

495 g picryl chloride and 121 g hydrochinone are dissolved in 3 l methylacetate and mixed with 240 ml triethylamine at a max. 30° C. under cooling with vigorous stirring. After distilling off the solvent in vacuum, the mass is first washed with warm ethanol, then with water. Yield of 1,4-(2',4',6'-trinitrophenoxy)benzene: 400 g (75% of theory).

EXAMPLE 11

(Nitration)

In this example, 10 g of each of the reaction products from Examples 4–6 were dissolved in 50 ml of fuming nitric acid and stirring for 1 hour at ambient temperature. Following this, the reaction mixture was poured into ½ liter of water, the solid component filtered out, washed and dried.

Yield: 11 g (93% of theory).

The resulting reaction products had the following properties:

| | Properties | | | | |
|---|---|---|---|---|---|
| | F | Vp | Friction Sensitivity | Percussion | EW |
| Compound | (°C.) | (°C.) | (N) | (J) | (J/g) |
| From Examples 4 and 6 | 277–279 | 283 | >350 | 5 | 3120 |
| From Example 5 | 277–279 | 315 | >350 | 5 | 3200 |

EXAMPLE 12

(Nitration)

In this example, 250 ml of fuming nitric acid was added to 250 ml concentrated sulfuric acid while stirring. Then, in each procedure, 50 g of the reaction products from Examples 1 to 3 were each introduced into the warm acid mixture and the suspension was simmered for 1 to 6 hours long. After cooling down, the solid component was filtered out, the residue washed free of acid with water and allowed to stand for 12 hours in a 2.5% NaHCO$_3$ solution. It was then filtered out, washed and dried.

Yield: 35–40 g (60–68.4% of theory).

The nitration products have the following properties:

| | Properties | | | | |
|---|---|---|---|---|---|
| Nitration | F | Vp | Friction Sensitivity | Percussion | EW |
| product | (°C.) | (°C.) | (N) | (J) | (J/g) |
| From Example 1 | 325 | 300–305 | >350 | 3 | 3560 |
| From Example 2 | 284–286 | 270–278 | >350 | 3 | 3350 |
| From Example 3 | >350 | 313–325 | >350 | 4 | 3300 |

EXAMPLE 13

The method is used as described in Examples 2 and 3 although using 1,3-dichloro-2,4,6-trinitro benzene and there are obtained polymers with a molar ratio of styphnic acid dichloride/dihydroxy benzene of 1:1.1. As with Example 8, these are nitrated for 30 minutes and then result in reactive polynitropolyphenylene oxides. The m-linked product has a Vp of 178° C.; whereas the p-linked product has a Vp of 213° C., EW 2793 J/g. The average molecular weight amounts to about 2400. The nitration reaction can, with larger batches and/or with a poor mixing of components, result in self-ignition with a vigorous combustion. For this reason, the procedures should preferentially be according to Example 10.

Example 14

(Nitration)

In this example, 50 g of the polymer from the reaction of 1,3-dichloro-2,4,6-trinitro benzene with hydrochinone (as described according to Example 9) are suspended in 400 ml of conc. sulfuric acid and mixed while stirring vigorously initially adding, drop-by-drop, with 250 ml of fuming nitric acid at a temperature of max. 30° C. It is left to react for one-half hour. The solid component is filtered out after being added to 5 liters of water, washed with water and dried. Yield: 50 g; Vp 244° C., EW 2738 J/g.

EXAMPLE 15

The reaction according to Example 3, although with use of 312 g 2,4,6-trinitro-3,5-dichloro anisole, instead of the styphic acid dichloride in the molar ratio 1:1.1 referred to hydrochinone, supplies 310 g of a polymer with a deflagration point of 210° C.

EXAMPLE 16

The nitration of 50 g of the polymer from Example 15 according to Example 14 results in 50 g of a substance with a deflagration point of 240° C.

EXAMPLE 17

Pyridine (8 ml) is added, drop-by-drop, while stirring at a temperature of 20° C. to a solution of 10 g 3,3'-dichloro-2,4,6,2',4'6'-hexanitrodiphenyl and 15 g 4-nitrophenol in 200 ml of acetone. Subsequently, the batch is poured into 2 liters of water and the solid component is separated out and then washed with water and ethanol. The yield is 18 g of a substance which softens starting at 108° C.

EXAMPLE 18

The nitration of 50 g of the substance from Example 17, according to Example 12, leads to 40 g of a substance with a softening point of 170° C. and a deflagration point of 252° C.

What is claimed is:

1. A nucleus-nitrated aryl ether which has a decomposition temperature above 200° C. and which has the formula Ar'-O-Ar''-O-Ar' wherein Ar' represents a phenyl radical substituted by 3 nitro groups and free of other substituents; and Ar'' represents a non-substituted phenylene radical.

2. A nucleus-nitrated aryl ether which has a decomposition temperature above 200° C. and which has the recurring unit —Ar'-O-Ar''-O—$_n$ wherein Ar' represents a phenylene radical substituted by 1 to 3 nitro groups and free of other substituents and Ar'' represents a non-substituted phenylene radical, when Ar' represents a phenylene radical substituted by three nitro groups, or a phenylene radical substituted by 1 to 3 nitro groups, when Ar' represents a phenylene group substituted by less than 3 nitro groups; and wherein n is an integer of from 4 to 20.

* * * * *